United States Patent
Haney et al.

(10) Patent No.: US 8,007,668 B2
(45) Date of Patent: Aug. 30, 2011

(54) DIALYSIS DEVICE WITH ACCESS PORT

(75) Inventors: Paul J. Haney, Beloit, WI (US);
Michael Robert Johnston, Twin Lake, MI (US)

(73) Assignee: Pierce Biotechnology, Inc., Rockford, IL (US)

( * ) Notice: Subject to any disclaimer, the term of this patent is extended or adjusted under 35 U.S.C. 154(b) by 297 days.

(21) Appl. No.: 12/366,049

(22) Filed: Feb. 5, 2009

(65) Prior Publication Data

US 2009/0200225 A1 Aug. 13, 2009

Related U.S. Application Data (60) Provisional application No. 61/027,216, filed on Feb. 8, 2008.

(51) Int. Cl.
*B01D 61/24* (2006.01)
(52) U.S. Cl. .......... 210/232; 210/321.6; 210/242.1; 210/321.75; 210/321.84; 210/455; 210/477; 210/500.21; 220/222; 220/216
(58) Field of Classification Search .......... 210/321.6, 210/321.61, 321.72, 321.75, 321.84, 232, 210/455, 477, 242.1, 500.21, 644; 215/355; 220/216, 222, 560, DIG. 19; 422/512, 513, 422/521, 527, 534, 568, 570
See application file for complete search history.

(56) References Cited

U.S. PATENT DOCUMENTS

| | | | | |
|---|---|---|---|---|
| 4,187,893 A | * | 2/1980 | Bujan | 604/408 |
| 5,324,428 A | | 6/1994 | Flaherty | |
| 5,503,741 A | * | 4/1996 | Clark | 210/232 |
| 5,783,075 A | | 7/1998 | Eddleman et al. | |
| 6,245,056 B1 | * | 6/2001 | Walker et al. | 604/539 |
| 6,531,061 B1 | * | 3/2003 | Cholewa | 210/232 |
| 7,056,440 B2 | * | 6/2006 | Haney et al. | 210/644 |
| 2005/0092666 A1 | | 5/2005 | Wilson | |

FOREIGN PATENT DOCUMENTS

| | | |
|---|---|---|
| WO | 95/08385 | 3/1995 |
| WO | 2005/087353 | 9/2005 |

OTHER PUBLICATIONS

European Search Report, dated May 11, 2009, mailed May 18, 2009.

* cited by examiner

*Primary Examiner* — Tony G Soohoo
*Assistant Examiner* — David C Mellon
(74) *Attorney, Agent, or Firm* — Thompson Hine LLP (57) ABSTRACT

A device for dialysis of a sample includes a sample chamber formed by a gasket and dialysis membranes affixed to each side of the gasket in facing relationship. A housing supports the dialysis membranes and gasket. An air chamber causes the device to float in a generally upright position when the device is immersed in a dialysate. An access port is provided through the gasket and between the dialysis membranes. The access port is accessible from outside the housing and in communication with the sample chamber such that a dispensing end of a dispensing device can be inserted through the access port to dispense sample into the sample chamber. In one embodiment, the gasket is impermeable or essentially impermeable to the sample being dialyzed.

7 Claims, 9 Drawing Sheets

Fig. 15

DIALYSIS DEVICE WITH ACCESS PORT

RELATED APPLICATIONS

This application claims priority from U.S. Application Ser. No. 61/027,216 filed on Feb. 8, 2008, the entire text of which is expressly incorporated by reference herein.

TECHNICAL FIELD

A device for dialysis of small, fixed-volume samples.

BACKGROUND

Molecules having various molecular weights can be separated across a semi-permeable membrane. The membrane by virtue of its composition, and consequently its porosity, allows relatively smaller molecules, that is, equal to or less than a particular molecular weight cutoff, to pass through the membrane. Relatively larger molecules are unable to pass through the membrane. Such membrane systems are often used in laboratory research and commonly referred to as dialysis membranes. Common applications of dialysis membranes are: exchanging one sample buffer for another buffer, sample desalting, molecular separations, and sample concentration.

Some methods use a dialysis membrane as the sole molecular exchange between a sample and dialysate. A widely used research method ties or clamps one end of the dialysis membrane, in the shape of a tube, to form a sack. The sample is added to the interior of the dialysis membrane sack which is then tied or clamped at the non-tied end. The sack, now a closed vessel, is submerged into the dialysate. To improve the dialysis process in terms of handling, reliability and speed, a variety of devices have been designed to house the dialysis membrane.

SUMMARY

A device for the dialysis of a sample includes a sample chamber formed by a gasket and dialysis membranes affixed to each side of the gasket in facing relationship. A housing supports the dialysis membranes and gasket. An air chamber causes the device to float in a generally upright position when the device is immersed in a dialysate. An access port is provided through the gasket and between the dialysis membranes. The access port is accessible from outside the housing and in communication with the sample chamber such that a dispensing end of a dispensing device can be inserted through the access port to dispense sample into the sample chamber. In one embodiment, the gasket is impermeable or essentially impermeable to the sample being dialyzed.

DETAILED DESCRIPTION

A device for dialysis of a sample includes a sample chamber formed by a gasket and dialysis membranes affixed to each side of the gasket in facing relationship. A housing supports the dialysis membranes and gasket. An air chamber causes the device to float in a generally upright position when the device is immersed in a dialysate. An access port is provided through the gasket and between the dialysis membranes. The access port is accessible from outside the housing and in communication with the sample chamber such that a dispensing end of a dispensing device can be inserted through the access port to dispense sample into the sample chamber. In one embodiment the gasket is impermeable or essentially impermeable to the sample being dialyzed.

Figure 1:
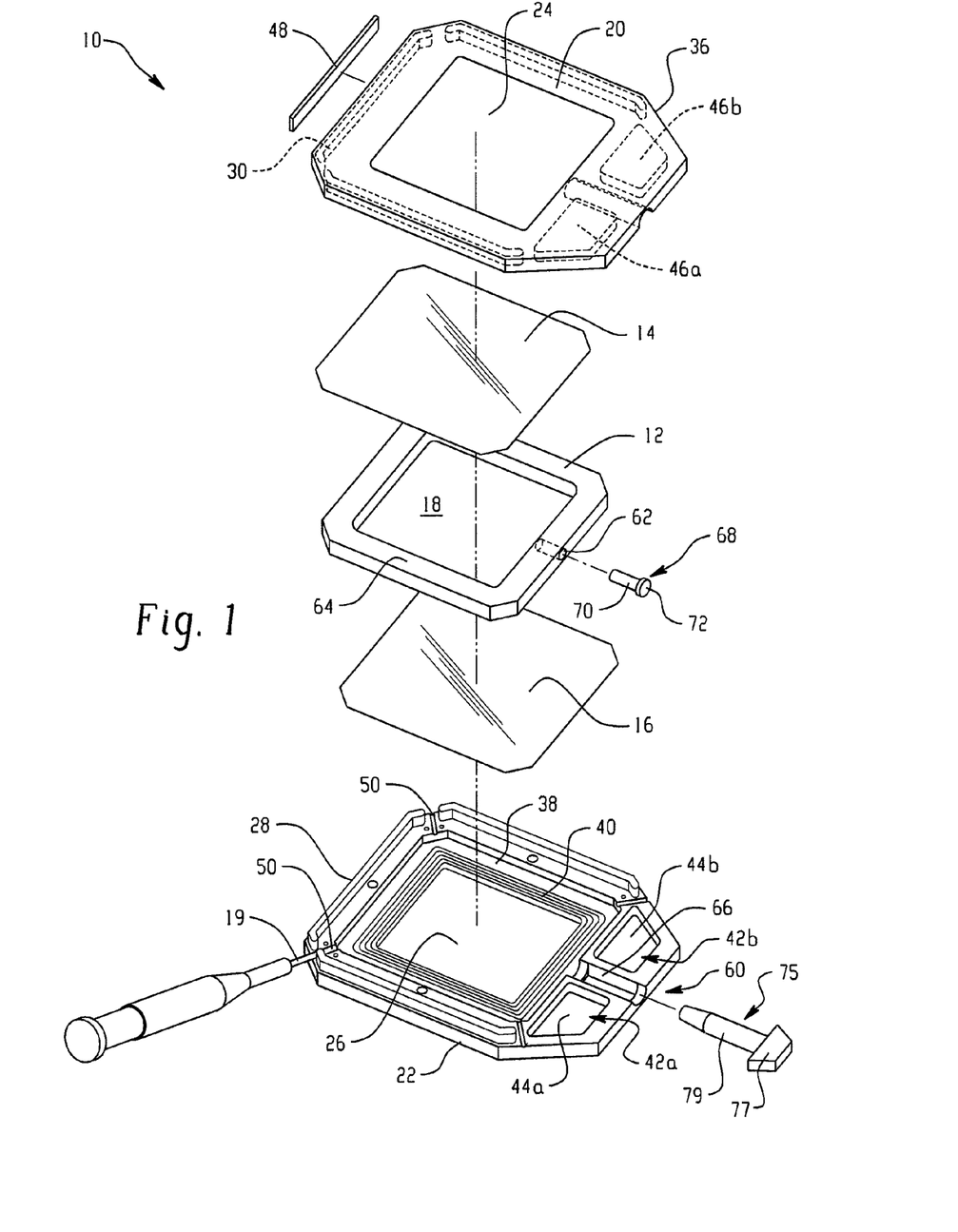
FIG. 1 is an exploded perspective view of an embodiment of a dialysis device.
Figure 2:
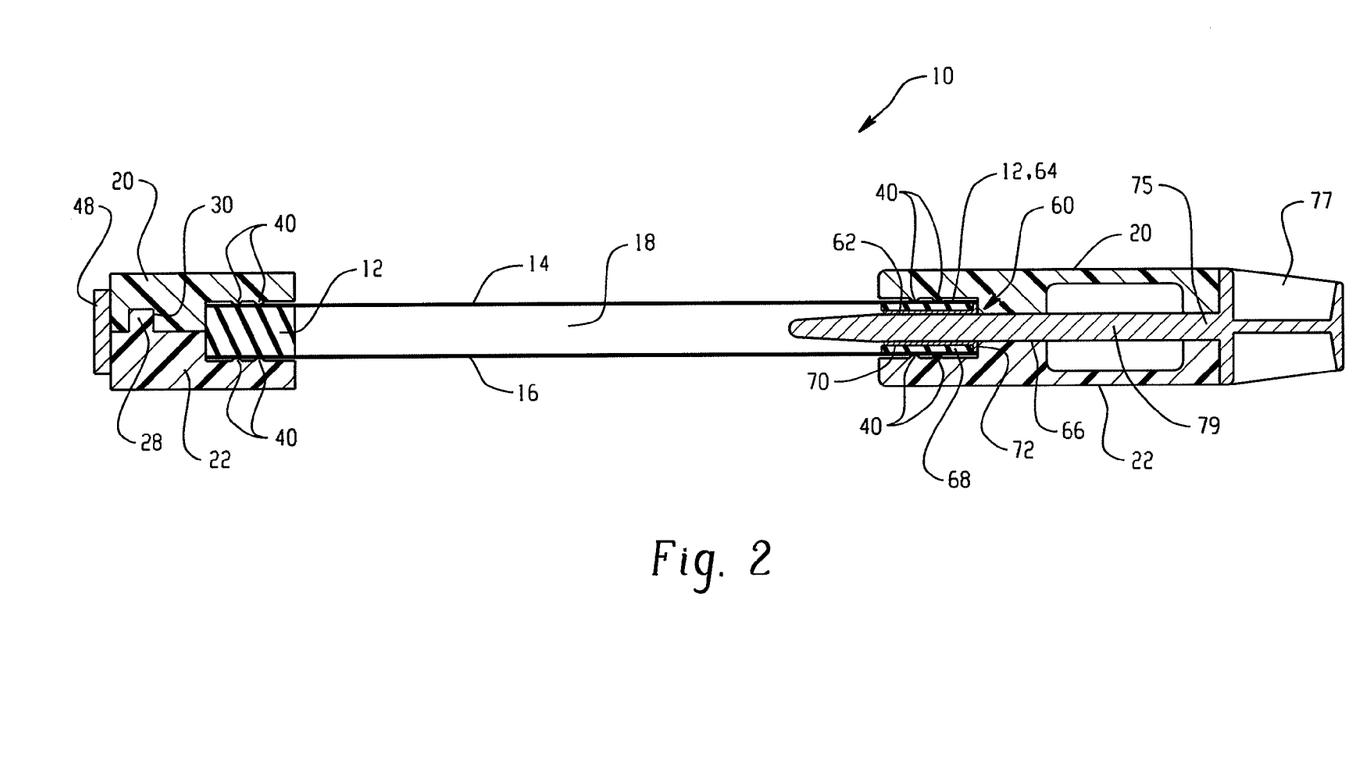
FIG. 2 is a side section view of the dialysis device of FIG. 1 in assembled form.

FIG. 1 illustrates an exploded view of a dialysis device, shown generally at 10. The device 10 includes a gasket 12 and a pair of dialysis membranes 14, 16. As illustrated by FIG. 2, the dialysis membranes 14, 16, once assembled, are affixed to each side of the gasket 12 to form a chamber 18 there between. The membranes 14, 16 are in a facing, substantially parallel relationship with respect to one another.

Referring to FIGS. 1 and 2, the chamber 18 formed by the membranes 14, 16 and the gasket 12 is sealed and the gasket 12 is capable of being penetrable by a sample introduction mechanism such as a syringe attached to a needle 19 or with a pipetting device through an access port 60. The needle 19 is inserted through the gasket 12 into the chamber 18 for delivery of sample, and then the syringe is withdrawn without sample being permitted to leak. To this end, the gasket 12 can be a material that is pliable with high memory function, for example, rubber, plastic, or silicone. For membranes 14, 16, customary dialysis membranes, commonly derived from regenerated cellulose, may be used. To achieve a sealed chamber, the membranes 14, 16 are securely affixed to the gasket 12 such as through the mechanism of adhesive bonding or a molding operation. Particular embodiments of the device may not require adhesive bonding or a molding operation due to the manner in which the device is constructed.

While the sealed chamber 18 formed by the gasket 12 and membranes 14, 16 can be directly used for dialyzing a sample, the device 10 includes a rigid housing formed by a pair of plates 20, 22. The housing structurally stabilizes the device 10, e.g., for facilitating handling. The housing also permits affixing identifying indicia and allows for directed needle insertion to minimize the probability of needle penetrations through the membranes 14, 16. Each plate 20, 22 contains windows 24, 26, respectively, positioned opposite the membranes 14, 16 of the device 10.

Alignment of the plates 20, 22 is achieved through a tongue 28 and groove 30 arrangement. Other arrangements are possible as known to a person of ordinary skill in the art. The plates 20, 22 are sealed to firmly sandwich the gasket 12 and membranes 14, 16 within the housing to form a completed device 10. Sealing may be accomplished by, e.g., sonic welding, adhesive, etc. as known to a person of ordinary skill in the art.

Each plate 20, 22 includes a ledge 36, 38, respectively, in which the gasket 12 resides in the completed device 10. To provide an enhanced, sealed chamber, each ledge 36, 38 includes one or more raised areas or pressure ridges 40 that in one embodiment are located along a central portion of each ledge 36, 38 for engaging the gasket 12 in the completed device 10. A pair of pressure ridges 40 extends along the periphery of each window 24, 26. Any desired number of pressure ridges 40 extending along the entire periphery may be used, or a portion of the periphery of each window 24, 26. For example, a larger number of pressure ridges 40 may provide greater protection against the transfer of fluid between each plate 20, 22 and the gasket 12. In addition, one or more pressure ridges 40 may be located on only one ledge, rather than both ledges. Other variations of the pressure ridges 40 are contemplated.

The completed device 10 includes air chambers 42a and 42b formed by each plate 20, 22 of the completed device 10. Specifically, each plate 20, 22 includes corresponding air pockets 44a, 44b and 46a, 46b, respectively, that together form the air chambers 42a and 42b when each plate 20, 22 is brought together to form the completed device 10. The air chambers 42a and 42b can be sealed by the plates 20, 22 by sonic welding, adhesive, etc. Thus, the air chambers 42a and 42b are integrally formed with the plates 20, 22.

In operation, the air chambers 42 cause the device 10 to float in an upright or vertical position when the completed device 10 is placed in a dialysate. In a some embodiments, the plates 20, 22 are formed from acrylonitride butadiene styrene (ABS) where the buoyancy characteristic of the plates 20, 22 allows the sample chamber 18 to be fully immersed in the dialysate, while the air chambers 42a and 42b keep the device 10 afloat. Other materials may be used to form the plates 20, 22, e.g., plastic or other polymeric material.

In one embodiment, a weight 48 is placed on an opposite end of the completed device 10 to that of the air chamber 42 to further assist in causing the device 10 to float in the upright position. The weight 48 should be sufficiently heavy to cause the completed device 10 to be suspended in the upright or vertical position in the dialysate, but not be so heavy such that the completed device 10 is completely submerged in the dialysate. The weight 48 is sufficiently heavy to cause the top of the completed device 10 to extend above the top of the dialysate so that the completed device 10 can be easily removed from the dialysate.

The housing, when assembled, contains one or more needle ports 50 for directing and guiding a needle into the gasket 12 and, in turn, the chamber 18. Each needle port 50 runs between the membranes 14, 16 and is substantially perpendicular to the edge of the gasket 12 so that the needle can access the chamber 18 without contacting either of the membranes 14, 16. Also, each needle port 50 is positioned higher in elevation than the pressure ridges 40 so that the needle can also access the chamber 18 without inadvertently contacting the pressure ridges 40. In some embodiments, as shown in FIG. 1, each needle port 50 meets the edge of the gasket 12 at a corner so that, by tilting the assembly 32, sample can be collected in the corner and withdrawn. The housing may be formed of a lightweight and durable material such plastic or other polymer that can be molded into the plates 20, 22 having the pressure ridges 40.

The access port (generally referred to as element 60) is provided at a top of the completed device 10. The access port 60 is provided through an opening 62 extending between the membranes 14, 16 and formed through a top wall 64 of the gasket 12, which is aligned with a channel 66 that runs between the air chambers 42a and 42b. The channel 66 is formed by and between each plate 20 and 22. In many embodiments, a sealing member 68, such as a sleeve, collar or retaining ring is located within the opening 62. The sealing member 68 includes a sleeve-shaped body portion 70 and a flanged portion 72 extending outwardly therefrom to inhibit movement of the sealing member into the gasket 12 once inserted into the opening 62. The sealing member 68 has a bore extending therethrough. In some embodiments, the bore has an inner diameter of at least about 1.3 mm, such as between about 1.3 mm and about 9 mm. However, the access port 60 or sealing member 68 is not limited to any particular sizes.

The sealing member 68 is formed of a material that is hard enough to maintain the opening 62, e.g., during assembly of the device 10, yet capable of achieving a suitable fluid-tight seal. The sealing member 68 may be friction fit within the opening 62, or an adhesive material may be used to adhere the sealing member within the opening 62 to inhibit its movement relative to the gasket 12. Suitable materials for forming the sealing member 68 are known to a person of ordinary skill in the art and include, e.g., nylon, polystyrene, etc.

A plug 75 is used to seal the access port 60. The plug 75 includes an enlarged head portion 77 and a plug portion 79 that can be inserted through the channel 66 and into the sealing member 68. The plug portion 79 and the sealing member 68 are sized to provide a fluid-tight seal once the plug portion is received within the sealing member. Friction between the plug portion 79 and the sealing member 68 inhibits removal of the plug 75 from the access port 60. The enlarged head portion 77 can be ergonomically shaped to allow for manual grasping and removal of the plug 75 from the access port 60 by a user. Suitable materials for forming the plug 75 include nylon, polystyrene, etc. In other embodiments, matching threads could be utilized on the plug portion 79 and sealing member 68 to provide a fluid tight seal.

The gasket 12 includes the opening 62, which is always present as compared to an opening formed through the gasket due to insertion of a needle through the needle ports 50. The opening 62, and opening through the sealing member 68, are closed and sealed using the plug 75. Additionally, the channel 66 is larger than the needle ports 50. In some embodiments, the channel 66 has a diameter that is at least two times (e.g., at least five times) larger than the diameter of the needle ports 50. This larger diameter of the channel 66 allows use of instruments, such as pipettes or other devices, having a dispensing end that is too large for penetrating the gasket 12 without damaging the gasket. Once a sample is dispensed into the chamber 18 through the access port 60 in communication therewith, the plug 75 is inserted into the access port such that the plug portion 79 seals with the sealing member 68.

An example of the use of the device 10 described above would be the exchange of a buffer, in which a protein sample resided, for another buffer. The protein in buffer "A" would be injected into the sealed sample chamber of the device and, then the device 10 would be submerged (weight 48 end first) into buffer "B" (dialysate) that is contained in a vessel, such as a beaker, such that the air chambers 42a and 42b cause the assembly to float in the dialysate. The protein, having a molecular weight greater than the dialysis membrane pores, is retained within the sample chamber 18, while the buffer within the sample chamber 18 exchanges by diffusion with the buffer in the dialysate.

The completed device 10 described herein is easily handled by the user and requires no special skill. Samples are loaded and unloaded with a needle and syringe through the needle ports 50 and/or with a larger dispensing device, such as a pipette, through access port 60. During the process, fingers need not contact the membranes 14, 16, only the housing surrounding the membranes 14, 16. The larger diameter of the access port 60 may be suitable for relatively large capacity devices 10, such as 30 ml devices or larger. In one embodiment, the access port 60 may be provided for smaller capacity devices, such as between 5 ml and 30 ml. The housing surrounding the sample chamber 18 is of ample size that allows for easy labeling of the sample with commonly used scientific marking pens. The rigidity of the housing positions the membranes 14, 16 so that they are parallel to each other and separated only by the thickness of the gasket 12. The result is that the sample chamber 18 of the device 10 has a high surface to volume ratio. Compared to dialysis tubing, which assumes a cylindrical shape when loaded with sample, the higher surface to volume of the device 10 results in faster dialysis times.

Figure 3:
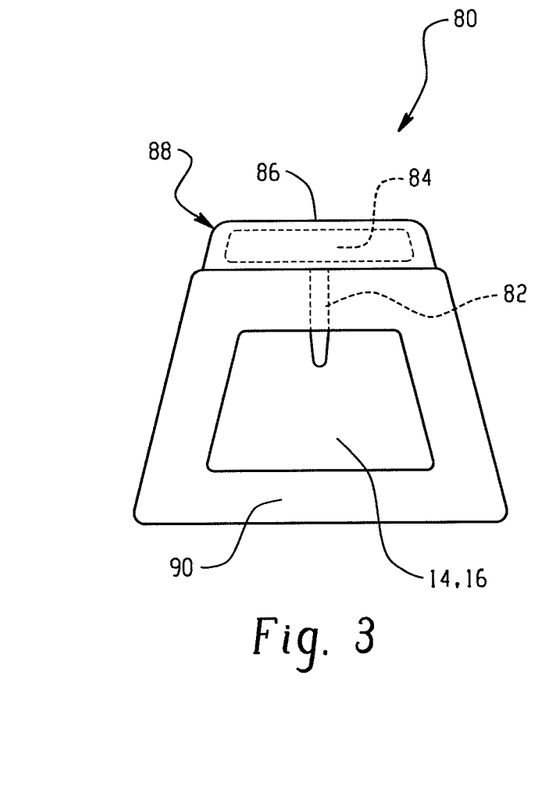
FIG. 3 is a front view of another embodiment of a dialysis device.

Referring to FIG. 3, another dialysis device embodiment 80 includes many of the features described above with respect to FIGS. 1 and 2 including an access port (represented by dashed lines 82). In this embodiment, an air chamber (represented by dashed lines 84) is formed in a head portion 86 of plug 88 rather than in a housing 90 of the device 80 between which the membranes 14 and 16 are held. In this embodiment, the air chamber 84 is removable from the housing 90 when the plug 88 is removed from the access port 82. The air chamber 84 causes the device 10 to float in an upright or vertical position when the device 80 is placed in a dialysate (not shown) and the plug 88 is secured in the access port 82.

Figure 4:
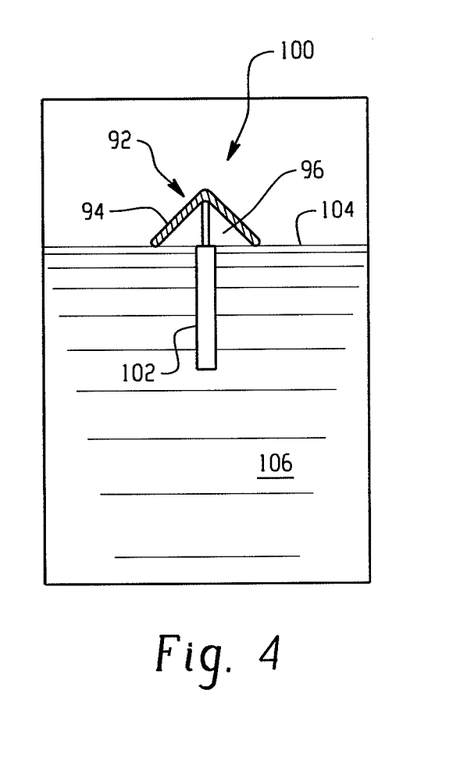
FIG. 4 is a side view of another embodiment of a dialysis device.
Figure 5:
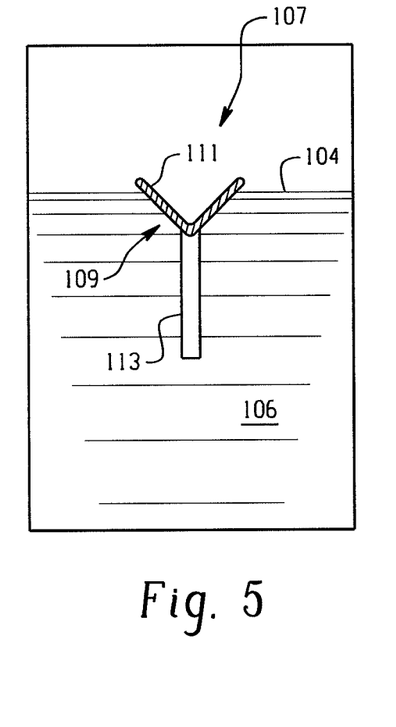
FIG. 5 is a side view of another embodiment of a dialysis device.

Referring to FIG. 4, the head portion of the plug may be of any suitable shape. In the embodiment of FIG. 4, a plug 92 includes a boat-shaped head portion 94 (shown in section). The head portion 94 captures a pocket of air in an air chamber 96 between the head portion and surface 104 of dialysate 106 such that the head portion 94 remains afloat with the housing 102 of the dialysis device 100 submerged. FIG. 5 shows a dialysis device 107 including a plug 109 having a boat-shaped head portion 111 (shown in section) floating upright on the surface 104 of the dialysate 106. The head portion 109 displaces the dialysate 106 such that it remains afloat with the housing 113 submerged.

Figure 6:
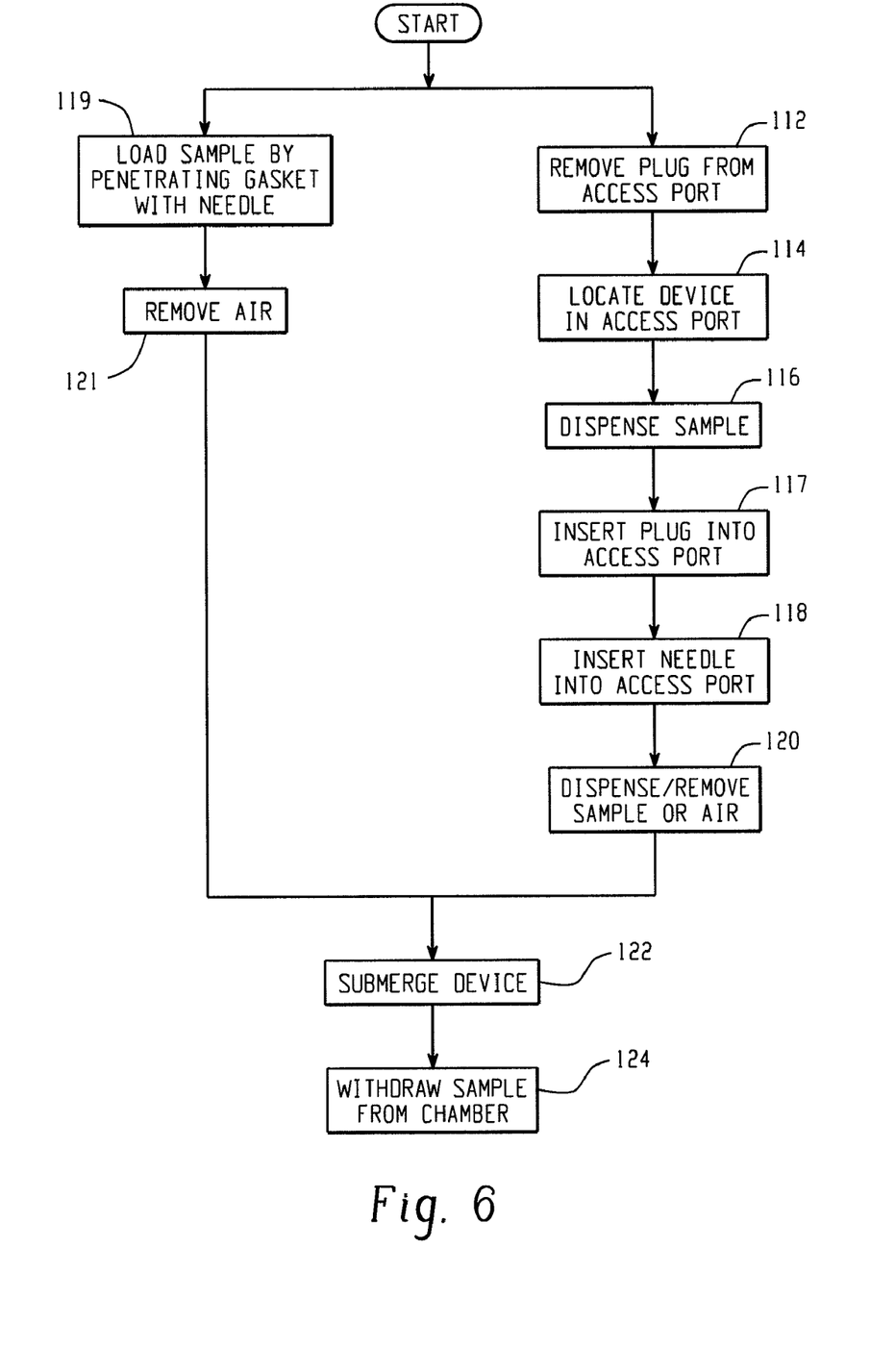
FIG. 6 illustrates an embodiment of a method of using the dialysis device of FIG. 1.
Figure 7:
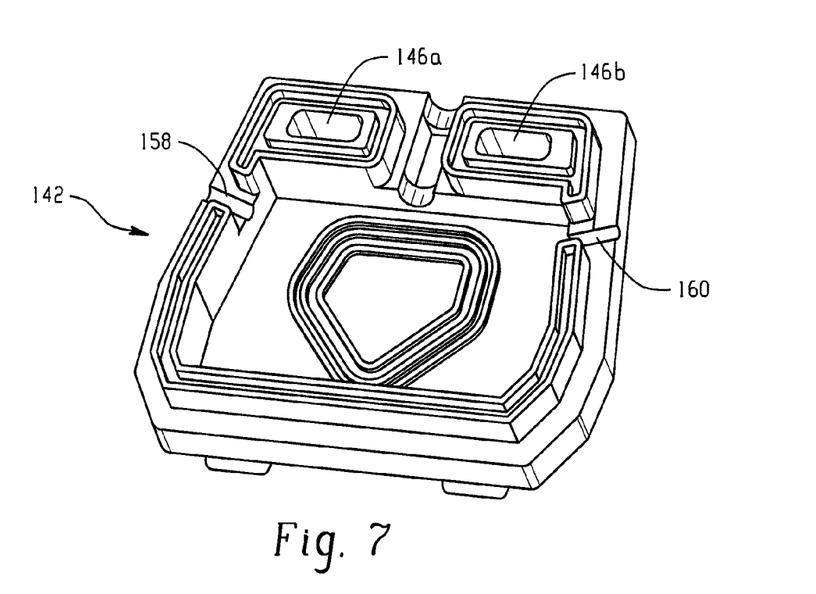
FIGS. 7-10 illustrate another embodiment of a dialysis device.
Figure 8:
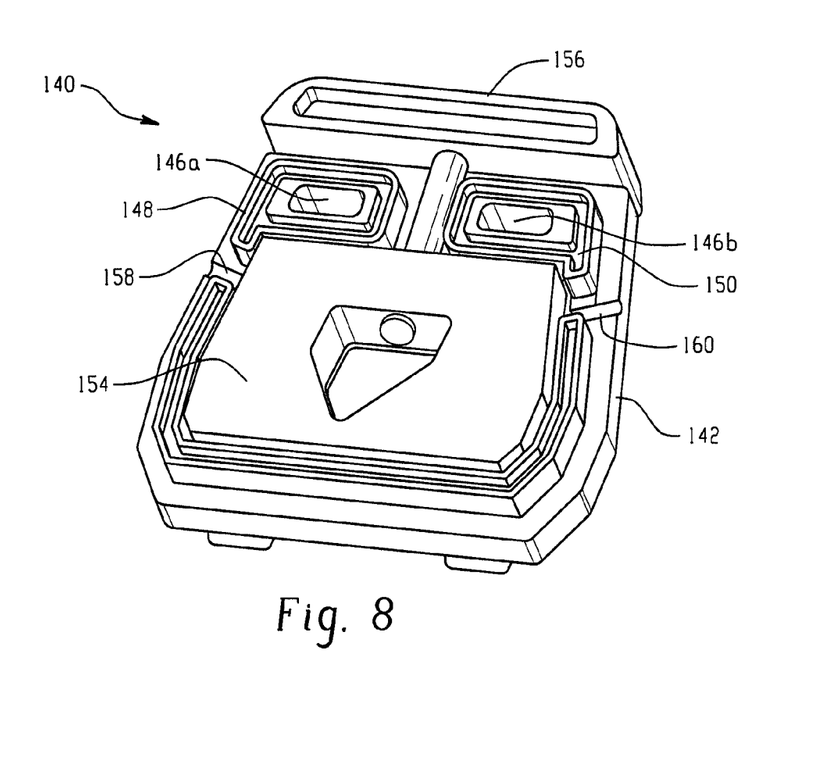
Figure 9:
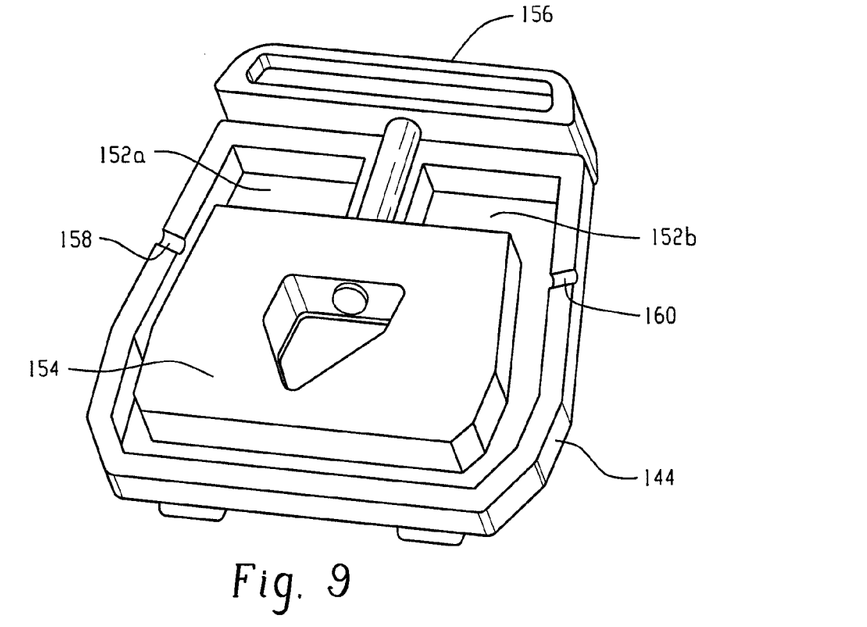
Figure 10:
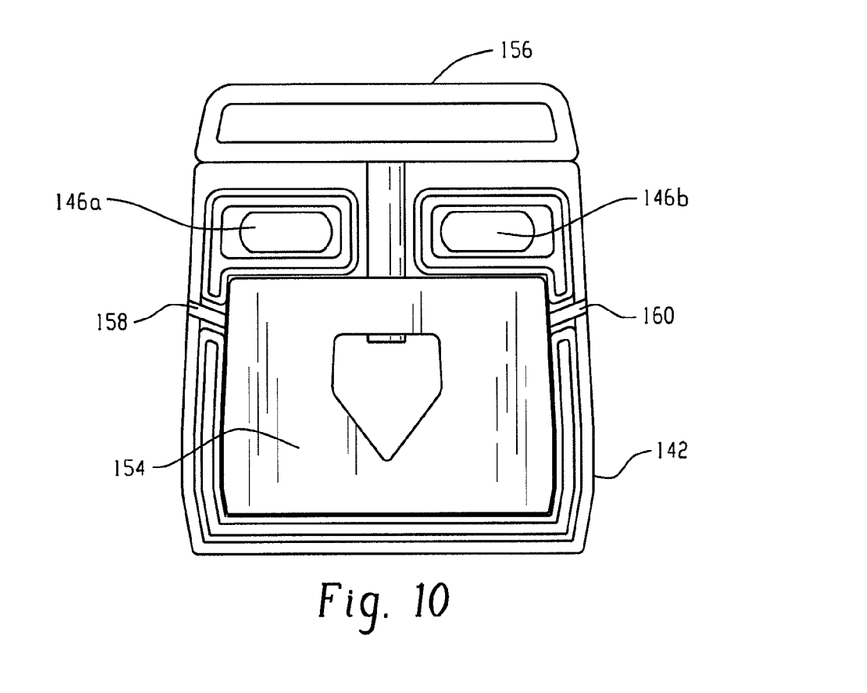
Figure 11:
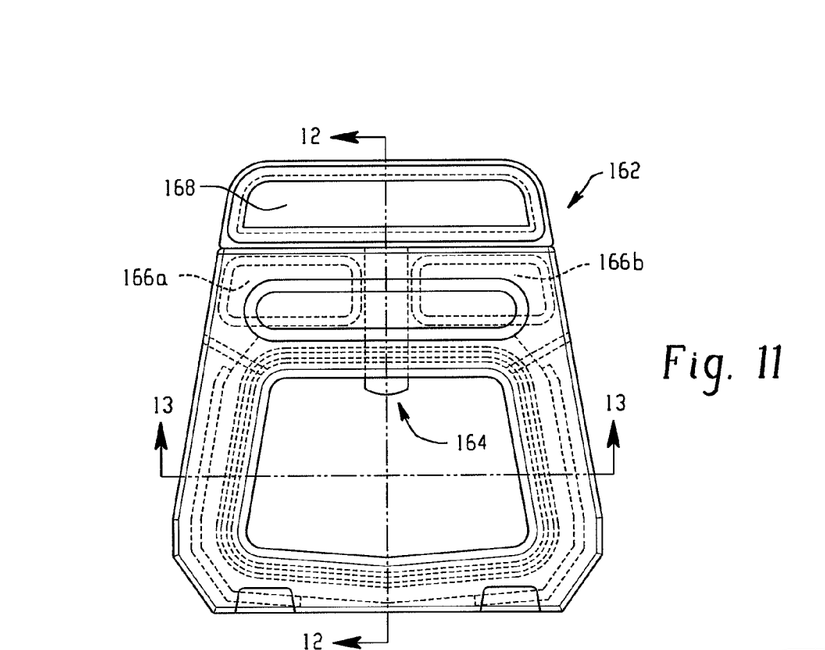
FIGS. 11-14 illustrate various views of another embodiment of a dialysis device.
Figure 12:
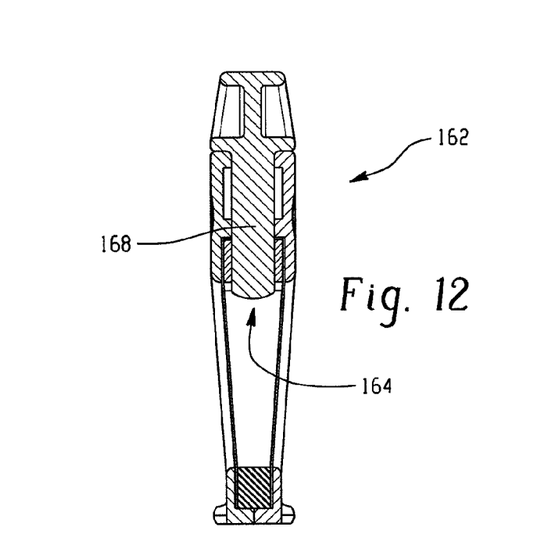
Figure 13:
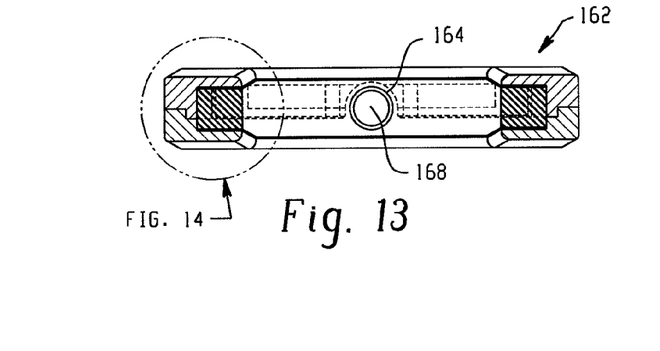
Figure 14:
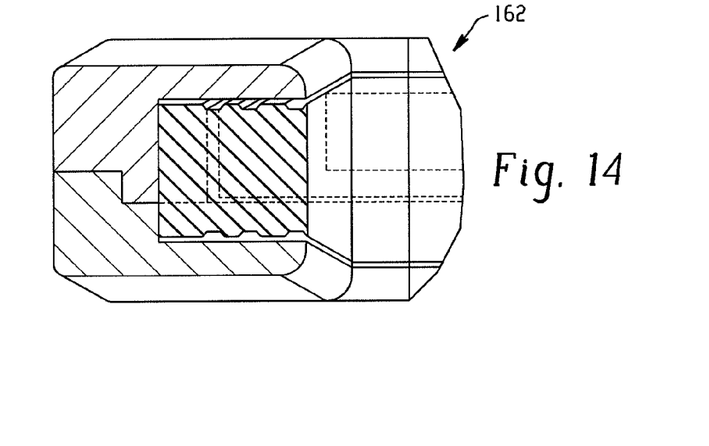

FIG. 6 illustrates a method 110 of using the devices including access ports for sample dialysis. The dialysis device described above provides a number of options for loading sample into the chamber. If, for example, a pipette is to be used, at step 112, the plug is removed from the access port to expose the access port. The sample is loaded into the device by sliding the dispensing device through the access port and into the chamber formed between the membranes at step 114. Once a dispensing end of the dispensing device enters the chamber, the sample is dispensed at step 116. At step 117, the plug portion of the plug is inserted through the access opening until it frictionally engages the sealing member to form a fluid-tight seal. In some instances, a needle may be inserted through one of the needle ports and through the side of the wall of the gasket at step 118, which also serves the function of a self-sealing septum. Once the needle passes through the gasket wall and penetrates the sample chamber, the plunger of the syringe is depressed at step 120 and sample transferred from the barrel of the syringe into the sample chamber. In some embodiments, the plunger may be pulled to remove air or sample at step 120.

If, for example, a syringe is to be used, at step 119, the sample is loaded into the device by sliding a needle through one of the needle ports through the side of the gasket, which also serves as a self-sealing septum. Once the needle passes through the gasket wall and penetrates into the sample chamber, the plunger of the syringe is depressed and the sample is transferred into the sample chamber at step 121.

At step 122, the device is submerged into the dialysate. In some embodiments, the end of the device having the weight is first immersed in the dialysate such that the device is in an upright position and the top of the device extends above the dialysate. In this manner, the device can be easily removed from the dialysate by grasping the head portion of the plug. The dialysate is held in a vessel, such as a beaker, and mixing of the dialysate can be incorporated to insure all dialysate contacts the membranes. Because of the devices self-contained nature it can easily be transferred to a vessel containing fresh dialysate which has the effect of accelerating the dialysis. Alternatively, the device can be pulled from the dialysate while it is poured from the vessel and fresh dialysate added. After sample dialysis is complete, the device is removed from the vessel containing the dialysate.

At step 124, the sample can be removed from the chamber using a syringe (e.g., by inserting through one of the needle ports) or another device (e.g., by inserting through the access port) and drawing the sample from the chamber.

FIGS. 7-10 illustrate another housing embodiment for a dialysis device 140 including plates 142 and 144. The first plate 142 includes air pockets 146*a* and 146*b*, each formed between a raised ridge 148 having a recessed channel 150 extending alongwith. The raised ridges 148 are received within pockets 152*a* and 152*b* to form air chambers 154*a* and 154*b* with a gasket 154 located between the plates 142 and 144. As above, the gasket 154 includes an opening with a sealing member located therein. A plug 156 is used to seal the opening. Two needle ports 158, 160 are provided through the sides of the housing and between the plates 142 and 144. The plates 142 and 144 can be connected by means of sonic welding, adhesive or the like.

FIGS. 11-14 illustrate various views of another dialysis device 162 having features similar to those described above including an access port 164, air chambers 166*a* and 166*b* and plug 168.

Figure 15:
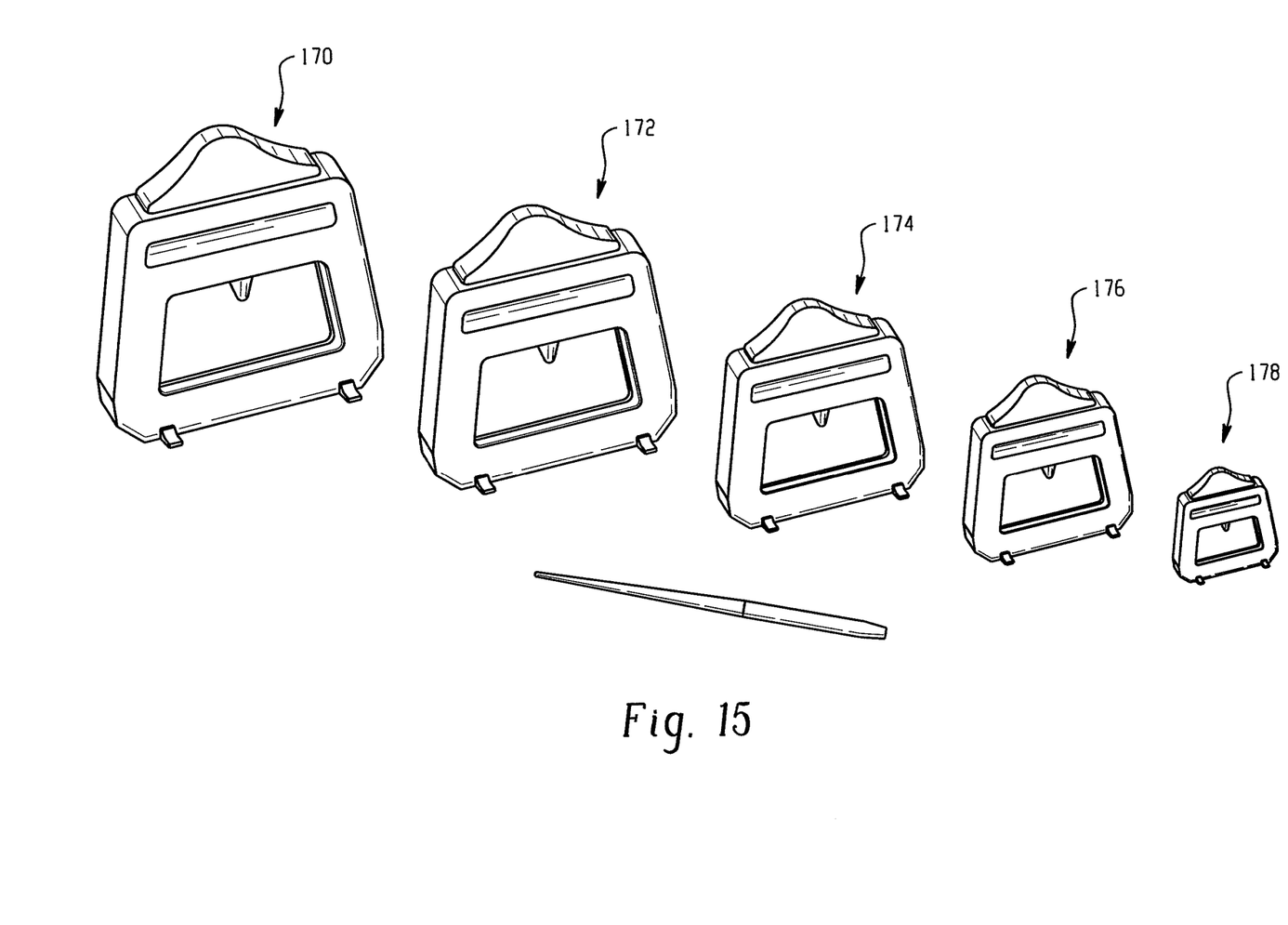
FIG. 15 illustrates a number of dialysis devices of various sizes.

FIG. 15 illustrates a number of dialysis devices 170, 172, 174, 176 and 178 of various sizes. Each dialysis device includes an access opening and plug, as described above. The dialysis devices can be sized to accommodate any number of sample volumes, such as between about 0.1 ml and about 1 ml in one embodiment, and about 60 ml and about 120 ml in another embodiment. However, the total size or contained volume for a specific device is not limited to any particular size.

Figure 16:
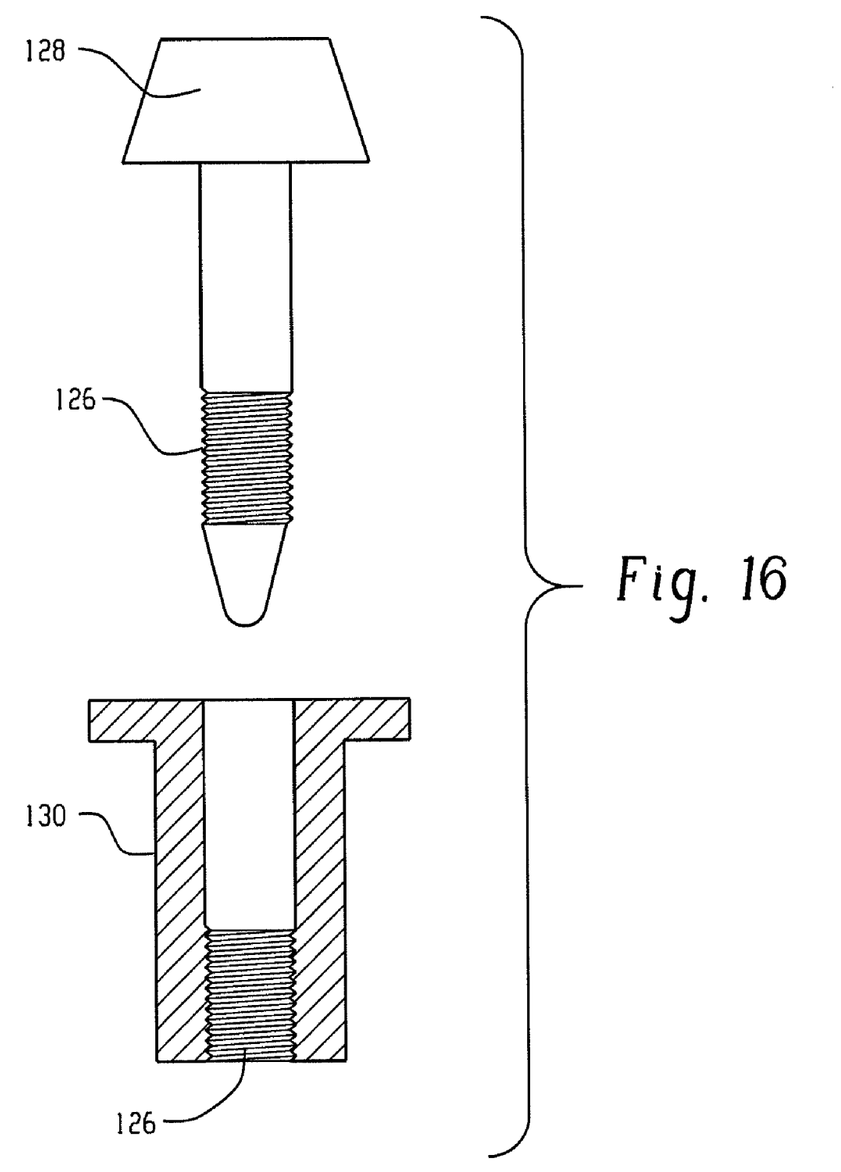
FIG. 16 illustrates an alternative connection for closing and sealing an access port of the dialysis device of FIG. 1.

The above summary, drawings, and description is intended by way of illustration and example only and is not intended to be limiting. For example, referring to FIG. 16, connections other than a friction-type fit between the plug and sealing member can be used to both secure the plug and sealing member together and form the fluid-tight seal. FIG. 16 illustrates a threaded connection 126 between a plug 128 and a sealing member 130 for sealing the access port. Further, while the access port is shown at the top of the dialysis devices described above, it may be located at the sides or bottom. Instead of a sealing member, other methods may be used to maintain the access opening in the gasket to form a seal, such as a resin or other coating-type material applied within the opening through the gasket along the inner wall. The resin or other coating-type material can harden and form a seal with the plug to seal the opening. In some embodiments, no sealing member is used and the plug forms a suitable fluid-tight seal against the inner wall of the opening through the gasket. During assembly, the plug may be inserted in the opening through the gasket to maintain the opening while the housing is welded together as described above without use of the sealing member (see FIGS. 8-10 showing the plug inserted in the gasket prior to full assembly). Inserting the plug into the opening through the gasket during assembly maintains the opening such that the plug may be inserted and removed repeatedly therefrom once the device is assembled. Additionally, the housing may not include needle ports and may only include the access port. Accordingly, other changes and modifications could be made.

What is claimed is:

1. A device for the dialysis of a sample, the device comprising:
 a sample chamber formed by a gasket and dialysis membranes affixed to each side of the gasket in facing relationship;
 a housing that supports the dialysis membranes and gasket;
 an air chamber that causes the device to float in a generally upright position when the device is immersed in a dialysate;
 an access port provided through the gasket and between the dialysis membranes, the access port accessible from outside the housing and in communication with the sample chamber such that a dispensing end of a dispensing device can be inserted through the access port to dispense sample into the sample chamber, and
 further comprising a sealing member, with an opening extending entirely therethrough, positioned in the access port, and a removable plug that is positionable in the sealing member to close and seal the access port.

2. The device of claim 1 wherein the gasket is penetrable and reusable such that a sample introduction mechanism can be inserted through the gasket into the sample chamber and then withdrawn without sample being permitted to leak.

3. The device of claim 1 wherein the plug includes a head portion and the air chamber is formed in the head portion.

4. The device of claim 1 further comprising a pair of plates that form the housing, the dialysis membranes and gasket being held between the pair of plates.

5. The device of claim 4 wherein the air chamber is formed between the pair of plates.

6. The device of claim 1 wherein the gasket is impermeable to the sample being dialyzed.

7. The device of claim 1 wherein the plug is removably positioned in the sealing member to close and seal the access port.

\* \* \* \* \*